(12) United States Patent
Wang et al.

(10) Patent No.: US 11,896,412 B2
(45) Date of Patent: Feb. 13, 2024

(54) COMPUTED TOMOGRAPHY SYSTEM AND METHOD AND DEVICE CONTROLLING THE POSITION OF THE X-RAY TUBE THEREOF

(71) Applicant: Siemens Healthcare GmbH, Erlangen (DE)

(72) Inventors: Ying Li Wang, Shanghai (CN); Jin Hua Ding, Shanghai (CN); Jian Zhang, Shanghai (CN); Jia Peng Zhu, Shanghai (CN)

(73) Assignee: Siemens Healthcare GmbH, Erlangen (DE)

( * ) Notice: Subject to any disclaimer, the term of this patent is extended or adjusted under 35 U.S.C. 154(b) by 135 days.

(21) Appl. No.: 17/534,509

(22) Filed: Nov. 24, 2021

(65) Prior Publication Data

US 2022/0160317 A1    May 26, 2022

(30) Foreign Application Priority Data

Nov. 25, 2020 (CN) .......................... 202011339298.0

(51) Int. Cl.
*A61B 6/00* (2006.01)
*A61B 6/03* (2006.01)

(52) U.S. Cl.
CPC ............ *A61B 6/4476* (2013.01); *A61B 6/032* (2013.01); *A61B 6/4435* (2013.01); *A61B 6/547* (2013.01); *A61B 6/582* (2013.01)

(58) Field of Classification Search
CPC ....... A61B 6/582; A61B 6/032; A61B 6/4476; A61B 6/4435; A61B 6/547; A61B 6/027; A61B 6/4014; A61B 6/04; A61B 6/482; A61B 6/566; A61B 6/037; A61B 6/0407; A61B 6/54; A61B 6/035; A61B 6/4429;
(Continued)

(56) References Cited

U.S. PATENT DOCUMENTS 5,175,754 A    12/1992   Casey et al.
6,553,091 B2 *  4/2003   Takanashi .............. A61B 6/035
                                                    378/207
(Continued)

FOREIGN PATENT DOCUMENTS

CN    107883913 A    4/2018
CN    110234275 A    9/2019
(Continued)

*Primary Examiner* — Irakli Kiknadze
(74) *Attorney, Agent, or Firm* — Banner & Witcoff Ltd.

(57) ABSTRACT

A method and a device of controlling the position of the X-ray tube of a computed tomography (CT) system may include: acquiring an AP signal output by an AP sensor of the CT system, an IP signal output by an IP sensor and encoder data output by a motor, determining a homing positioning signal $AP_0$ of the AP signal based on the AP signal and the IP signal, where the homing positioning signal $AP_0$ is used to determine the starting point of the period of rotation of the X-ray tube, utilizing the encoder data to calculate the encoder data containing AP signal based on the determined homing positioning signal $AP_0$, where the encoder data containing AP signal is the AP signal processed by use of the encoder data, and controlling the position of the X-ray tube based on the encoder data containing AP signal.

16 Claims, 3 Drawing Sheets

(58) Field of Classification Search
CPC ....... A61B 6/025; A61B 6/4452; A61B 6/545;
A61B 6/5294; A61B 6/5205; A61B
90/39; A61B 34/20; A61B 6/585; A61B
6/0457; A61B 6/56; A61B 6/504; A61B
6/5276; A61B 6/583; A61N 5/1049;
A61N 2005/1061; A61N 5/103; A61N
5/1081; A61N 5/1075; A61N 5/1045;
A61N 5/107; A61N 5/1071; A61N
5/1079; A61N 5/1048; A61N 5/1067;
A61N 2005/005; A61N 2005/1052; A61N
2005/1091; A61N 2005/1094; G21K
1/046; G01B 7/30; G01N 23/046

USPC ........................................................ 378/4, 15

See application file for complete search history.

(56) References Cited

U.S. PATENT DOCUMENTS

| 9,974,513 | B2* | 5/2018 | Hannemann | A61B 6/035 |
| 2001/0055362 | A1 | 12/2001 | Takanashi et al. | |
| 2006/0054798 | A1 | 3/2006 | Welker | |
| 2012/0209555 | A1* | 8/2012 | Tang | A61B 6/5205 378/15 |
| 2018/0085085 | A1 | 3/2018 | Hannemann | |
| 2018/0133518 | A1 | 5/2018 | Harper et al. | |

FOREIGN PATENT DOCUMENTS

| DE | 102004042486 A1 | 3/2006 |
| DE | 102016218888 B3 | 11/2017 |
| JP | 2011245195 A | 12/2011 |
| WO | 2016084567 A1 | 6/2016 |
| WO | 2018093933 A1 | 5/2018 |

* cited by examiner

FIG 4
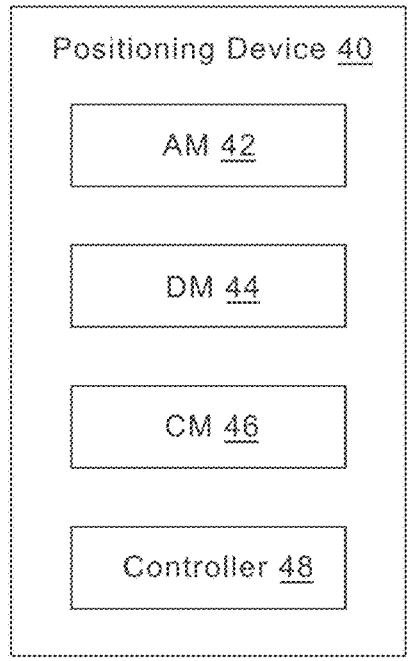
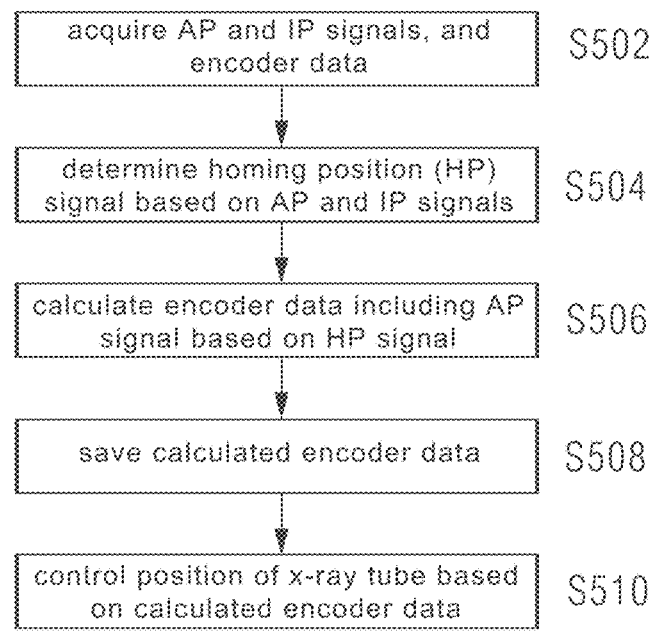
FIG 5

COMPUTED TOMOGRAPHY SYSTEM AND METHOD AND DEVICE CONTROLLING THE POSITION OF THE X-RAY TUBE THEREOF

CROSS REFERENCE TO RELATED APPLICATIONS

This patent application claims priority to Chinese Patent Application No. 202011339298.0, filed Nov. 25, 2020, which is incorporated herein by reference in its entirety.

BACKGROUND

Field

The disclosure relates to the technical field of medical devices, in particular to a method and a device of controlling the position of the X-ray tube in a computed tomography (CT) system, and a CT system.

Related Art

A CT system mainly comprises an X-ray tube, an X-ray detector array, a gantry and a patient bed. The X-ray tube and the X-ray detector array are disposed on the gantry rotating around the patient bed. Usually, the patient bed can move relative to the gantry. The X-ray tube generates a sector X-ray beam, and the X-ray beam passes one slice of an object (for example, a patient) which is being imaged and irradiates on the X-ray detector array. During CT imaging, the included angle between the X-ray beam and the body slice of the patient and the position of the patient bed relative to the gantry change continuously.

The angular position (AP) of the X-ray tube is a very important parameter of the CT system and affects the imaging quality of the CT system. Especially, if the patient needs to use CT for X-ray interventional therapy, it is necessary to precisely position the X-ray tube.

In order to obtain a precise angular position of the X-ray tube, a high-cost AP measurement system and a motor are adopted for a high-end CT system (for example, Definition system). Although a DC motor which can precisely position a sensor is used to acquire the precise position of the X-ray tube in a high-end CT system, it will take a lot of time and cost because the bearing needs to be assembled by use of DC driving. Usually, the minimum step of the position of the X-ray is 15 degrees and the accuracy is 2 degrees because of the limited number of check points in a low-end CT system. It is difficult to apply the interventional therapy in a low-end CT system because the low-end CT system cannot guarantee that the X-ray tube stops, with a step of 1 degree. No valid solution has been proposed for the above-mentioned problem.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

FIG. 4 shows a device for controlling the position of the X-ray tube of a CT system according to an exemplary embodiment of the disclosure.

FIG. 5 is a flowchart of the method of controlling the position of the X-ray tube of a CT system according to an exemplary embodiment of the disclosure.

Figure 1:
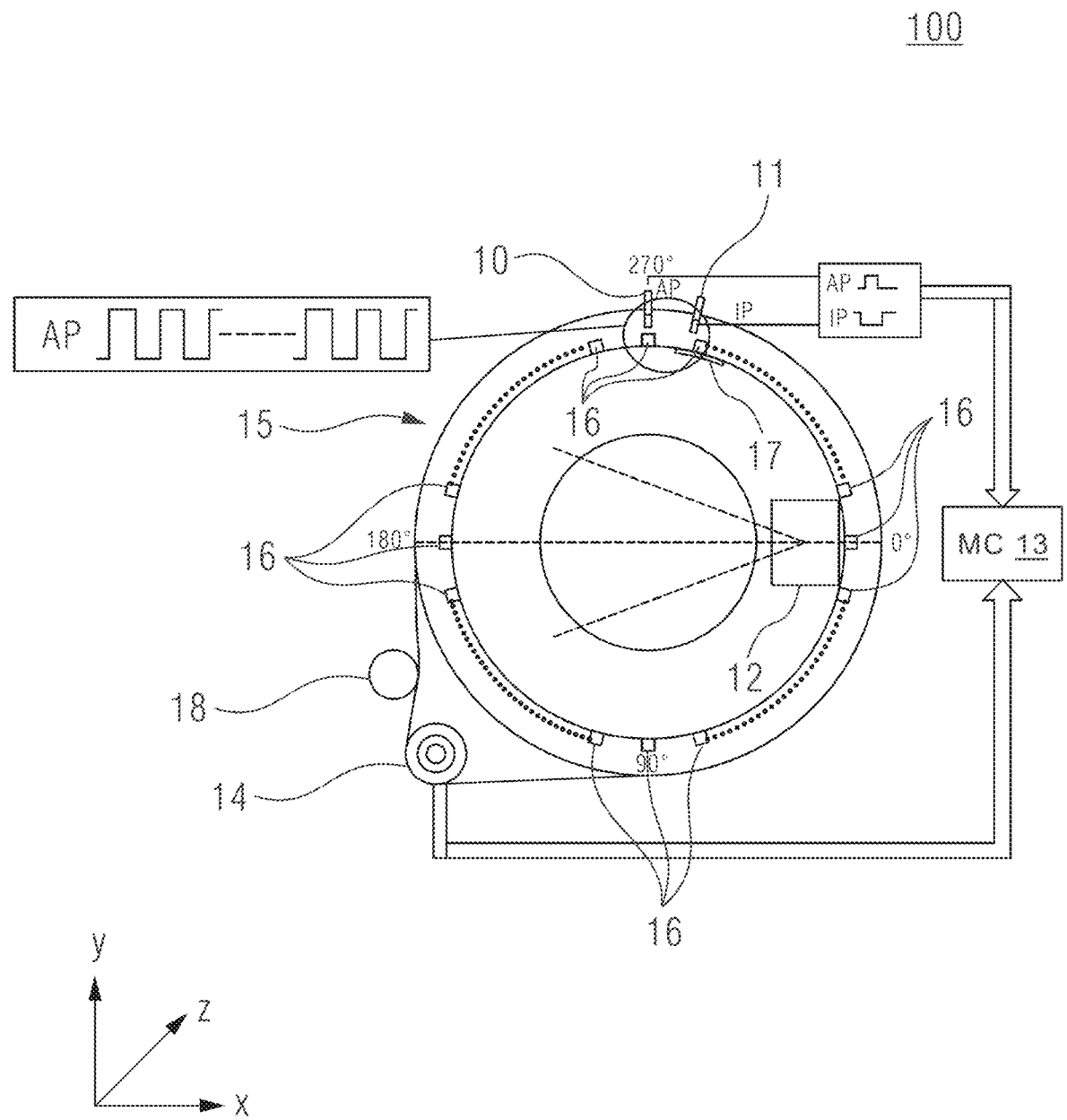
FIG. 1 shows a CT system according to an exemplary embodiment of the disclosure.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

According to one aspect of the embodiments of the disclosure, a method of controlling the position of the X-ray tube of a CT system is provided, and the method comprises: acquiring an AP signal output by an AP sensor of the CT system, an index pulse (IP) signal output by an IP sensor and encoder data output by a motor, determining a homing positioning signal $AP_0$ of the AP signal based on the AP signal and the IP signal, wherein the homing positioning signal $AP_0$ is used to determine the starting point of the period of rotation of the X-ray tube, utilizing the encoder data to calculate the encoder data containing AP signal based on the determined homing positioning signal $AP_0$, wherein the encoder data containing AP signal is the AP signal calibrated by use of the encoder data, and controlling the position of the X-ray tube based on the encoder data containing AP signal.

Through the above-mentioned method, the technical problem that the CT system cannot precisely control the position of the X-ray tube in the related technology is solved and the position of the X-ray tube can precisely be controlled.

In one exemplary embodiment of the disclosure, the AP signal is an angular position signal acquired after the AP sensor detects a plurality of check points arranged at even intervals on the outer circumferential surface of the gantry of the CT system, and/or the IP signal is an IP signal acquired after the IP sensor detects a reference check point arranged on the outer circumferential surface of the gantry of the CT system, and the IP signal is used to determine the period of rotation of the X-ray tube, and/or the encoder data is data output by the encoder of the motor and is used to control the speed of rotation of the X-ray tube.

Through the above-mentioned method a positioning calculation error caused by a belt slip is eliminated, and thus the positioning accuracy of the X-ray tube is improved.

In one exemplary embodiment of the disclosure, determining a homing positioning signal $AP_0$ of the AP signal based on the AP signal and the IP signal comprises: detecting whether the current IP signal is a high-level signal, and determining the high-level signal of the AP signal in the period in which the current IP signal is continuously a high-level signal to be the homing positioning signal $AP_0$ if the current IP signal is a high-level signal.

Through the above-mentioned method, the step positioning precision of the X-ray tube is increased to 1 degree, without any new component added.

In one exemplary embodiment of the disclosure, utilizing the encoder data to calculate the encoder data containing AP signal based on the determined homing positioning signal $AP_0$ comprises: detecting each high-level signal $AP_i$ of the AP signal in the period from the homing positioning signal $AP_0$ to when the IP signal is a high-level signal again, respectively calculating the pulse count of the encoder data in the time segment between the homing positioning signal $AP_0$ and each high-level signal $AP_i$, and saving the correspondence between the calculated pulse count of the encoder data and the AP signal as an encoder data containing AP signal.

Through the above-mentioned method, the correspondence between an AP signal and encoder data can more precisely be calculated, and thus making it possible to precisely position the X-ray tube.

In an exemplary embodiment of the disclosure, controlling the position of the X-ray tube based on the encoder data containing AP signal comprises: reading the saved encoder data containing AP signal during the rotation of the gantry of the CT system, and utilizing the encoder data containing AP signal to calibrate the position of the X-ray tube so as to control the position of the X-ray tube.

Through the above-mentioned method, without any sensing device or component added, the position of the X-ray tube is calibrated by use of the pre-adjustment mode during the subsequent operation, and thus the precision of positioning the X-ray tube is improved.

According to another aspect of the embodiments of the disclosure, a device of controlling the position of the X-ray tube of a CT system is provided, and the device comprises: an acquisition module, configured to acquire an AP signal output by an AP sensor of the CT system, an IP signal output by an IP sensor and encoder data output by a motor, a determination module, configured to determine a homing positioning signal $AP_0$ of the AP signal based on the AP signal and the IP signal, wherein the homing positioning signal $AP_0$ is used to determine the starting point of the period of rotation of the X-ray tube, a calculation module, configured to utilize the encoder data to calculate the encoder data containing AP signal based on the determined homing positioning signal $AP_0$, wherein the encoder data containing AP signal is the AP signal calibrated by use of the encoder data, and a controller, configured to control the position of the X-ray tube based on the encoder data containing AP signal.

Through the above-mentioned structure, the technical problem that the CT system cannot precisely control the position of the X-ray tube in the related technology is solved and the position of the X-ray tube can precisely be controlled.

In one exemplary embodiment of the disclosure, the determination module is further configured to detect whether the current IP signal is a high-level signal, and determine the high-level signal of the AP signal in the period in which the current IP signal is continuously a high-level signal to be the homing positioning signal $AP_0$ if the current IP signal is a high-level signal.

Through the above-mentioned structure, the step positioning precision of the X-ray tube is increased to 1 degree, without any new component added.

In one exemplary embodiment of the disclosure, the calculation module is further configured to detect each high-level signal $AP_i$ of the AP signal in the period from the homing positioning signal $AP_0$ to when the IP signal is a high-level signal again, respectively calculate the pulse count of the encoder data in the time segment between the homing positioning signal $AP_0$ and each high-level signal $AP_i$, and save the correspondence between the calculated pulse count of the encoder data and the AP signal as an encoder data containing AP signal.

Through the above-mentioned structure, the correspondence between an AP signal and encoder data can more precisely be calculated, and thus making it possible to precisely position the X-ray tube.

In one exemplary embodiment of the disclosure, the controller is further configured to read the saved encoder data containing AP signal during the rotation of the gantry of the CT system, and utilize the encoder data containing AP signal to calibrate the position of the X-ray tube so as to control the position of the X-ray tube.

Through the above-mentioned structure, without any sensing device or component added, the position of the X-ray tube is calibrated by use of the pre-adjustment mode during the subsequent operation, and thus the precision of positioning the X-ray tube is improved.

According to a further aspect of the disclosure, a CT system is provided and the CT system comprises: a gantry, an AP sensor, an IP sensor, a motor and a motor controller, wherein the AP sensor is configured to detect a plurality of check points arranged at even intervals on the outer circumferential surface of the gantry to acquire an AP signal, the IP sensor is configured to detect a reference check point arranged on the outer circumferential surface of the gantry to acquire an IP signal, the motor is configured to output encoder data of the motor, and the motor controller is implemented as the above-mentioned device.

Through the above-mentioned CT system, the technical problem that the CT system cannot precisely control the position of the X-ray tube in the related technology is solved and the position of the X-ray tube can precisely be controlled.

According to a fourth aspect of the disclosure, a computer-readable storage medium is provided, a computer instruction is stored in the computer-readable storage medium, and when executed, the instruction enables a processor to execute the above-mentioned method.

According to one exemplary embodiment of the disclosure, a CT system 100 is provided. As shown in FIG. 1, the CT system 100 comprises: an AP sensor 10, an IP sensor 11, an X-ray tube 12, a motor controller 13, a motor 14, a gantry 15, a plurality of check points 16, a reference check point 17, and a tension pulley 18.

The gantry 15 consists of two parts: a rotary component and a static component, wherein the rotary component can rotate around the central axis of the gantry 15 in the X-Y plane of the X, Y and Z axes of the rectangular coordinate system shown in FIG. 1, a plurality of check points 16 and a reference check point 17 are arranged on the outer circumferential surface of the rotary component, an X-ray tube 12 and a detector array are oppositely mounted on the inner circumference surface, an AP sensor 10 and an IP sensor 11 are arranged on the inner circumferential surface of the static component, and the two sensors are separated at a certain distance. A patient bed (not shown) is provided in the gantry 15, a patient can lie on the bed, and the bed can move in the Z-axis direction of the rectangular coordinate system. The rotary component of the gantry 15 can continuously rotate around the patient bed.

The X-ray tube 12 is disposed on the inner circumferential surface of the rotary component of the gantry 15 and emits a sector X-ray beam to the detector array (not shown) which is opposite to the X-ray tube 12 and is located on the other side of the inner circumferential surface of the rotary component. The X-ray beam emitted from the X-ray tube 12 hits the detector array after passing through a patient and attenuating. The strength of the attenuated radiation beam received at the detector array depends on the patient caused energy attenuation of the X-ray beam. Each detector element of the detector array generates an independent electrical signal, and the electrical signal represents the measured strength of the X-ray beam after the attenuation. After that, the measured strength of each detector of the detector array is collected, and the measured strength is an analog electrical signal. Therefore, it is usually necessary to further send the measured strength to an analog-to-digital converter which digitalizes analog signals for an analog-digital conversion. The image re-constructor (not shown) receives the sampled digital X-ray data from the analog-to-digital converter and performs a high-speed image reconstruction.

The AP sensor 10 and the IP sensor 11 are adjacently disposed on the inner circumferential surface of the static component of the gantry 15. The plurality of check points 16 are arranged at even intervals on the outer circumferential surface of the rotary component. In one exemplary embodiment of the disclosure, the AP sensor 10 and the IP sensor 11 are proximity switches, the check points 16 are metal heads, and the reference check point 17 is a metal groove. The proximity switch is a position switch which can be operated without any direct mechanical contact with a moving component. When an object (for example, check points 16 and reference check point 17) approaches the sensing surface of the switch to a detectable distance, the switch can act without any mechanical contact or any pressure exerted, and thus the position and stroke of a moving mechanism can accurately be reflected.

During the rotation of the gantry 15, when the distance between a check point 16 and the AP sensor 10 reaches a preset detectable distance, the AP sensor 10 will sense the check point 16, and the switch of the AP sensor 10 is in the ON state and outputs a high-level signal as a response signal; when the check point 16 departs from the AP sensor 10 and the distance away from the AP sensor 10 is greater than the preset detectable distance, the AP sensor 10 will fail to sense the check point and output a low-level signal Alike, when the distance between the reference check point 17 and the IP sensor 11 is less than a preset reference detectable distance, the IP sensor 11 outputs a high-level signal, and otherwise outputs a low-level signal all the time.

Figure 2:
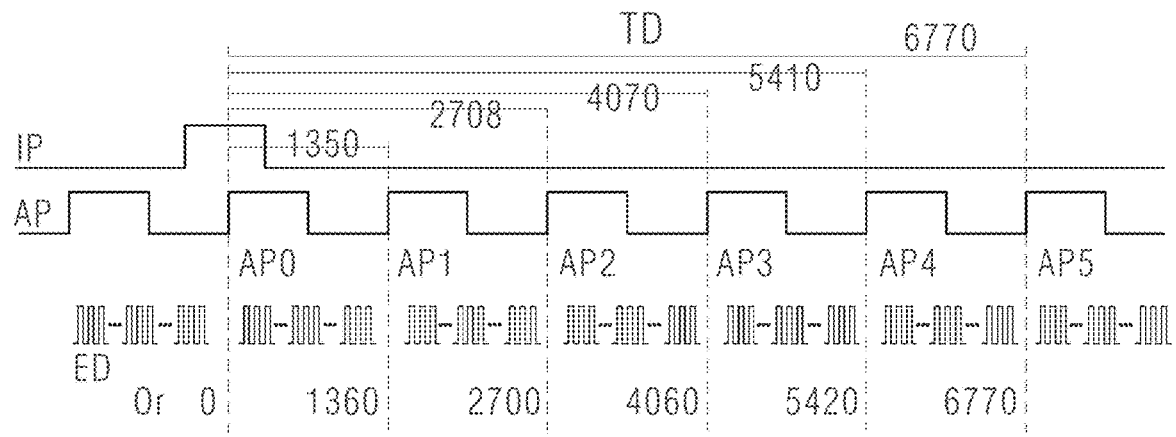
FIG. 2 shows a plot of a pulse signal according to an exemplary embodiment of the disclosure.

FIG. 2 shows the pulse signals generated by the IP sensor 11 and the AP sensor 10. When the X-ray tube 12 rotates once around the central axis of rotation of the gantry 15 along with the gantry 15, the IP sensor 11 generates only one pulse signal, namely, one high-level signal, while the AP sensor 10 generates a pulse train with a period T and the pulse train contains pulse signals whose number corresponds to the number of check points 16. The angle between every two check points 16 is determined by the number of check points 16. Supposing the number of check points 16 is n, the angle between every two check points 16 is 360/n degrees. From FIG. 2, it can be seen that the pulse width of an AP signal is different from that of an IP signal. Because the number of check points 16 is different from the number of reference check points 17, the durations of response signals are different.

In addition, since only one reference check point 17 is provided, there is only one chance that the distance between the reference check point 17 and the IP sensor 11 reaches the preset reference detectable distance when the gantry 15 rotates once. Thus, the preset reference detectable distance can be used as a flag indicating the gantry 15 or the X-ray tube 12 rotating once. Therefore, a response signal from the IP sensor 11 can be expressed by use of IP. In FIG. 1, when the X-ray tube 12 rotates clockwise from the 0° position, a response signal output from the AP sensor 10 is $AP_0$, and a response signal output from the IP sensor 11 is IP. Since the check points 16 are arranged at even intervals on the outer circumferential surface of the rotary component of the gantry 15, the check points 16 move toward the AP sensor 10 one by one at certain intervals. Therefore, the AP sensor 10 will generate n high-level signals in turn, wherein n is the number of the check points 16. Only a part of AP is shown in FIG. 2.

The motor 14 is configured to control the speed of rotation and direction of rotation of the gantry 15 under the control of the motor controller 13, and thus further control the position of the X-ray tube 12 disposed on the gantry 15. The motor 14 has an encoder. The encoder is usually an incremental encoder and the encoder data output by the encoder is mainly the pulse count per rotation. The pulse count of the encoder data is shown by ED in FIG. 2. The tension pulley 1819 is configured to control the degree of tightness of the belt connecting the gantry 15 and the motor 14.

The motor controller 13 controls the running of the motor 14 to control the position of the X-ray tube 12 based on the AP signal acquired from the AP sensor 10, the IP signal acquired from the IP sensor 11 and encoder data of the motor 14. The motor controller 13 may be a PC, a workstation or a central processing unit (CPU) embedded in the CT system. In other embodiments of the disclosure, the motor controller 13 may also be a more advanced processing system, for example, a distributed processing system.

The motor controller 13 utilizes the IP signal acquired from the IP sensor 11 and the AP signal acquired from the AP sensor 10 to calculate the homing positioning signal of the X-ray tube 12, that is to say, to find the $AP_0$ signal. After determining the $AP_0$ signal, the motor controller 13 utilizes the encoder data to calculate the pulse count of encoder data between AP signals, starting from $AP_0$. As shown in FIG. 2, the pulse count of encoder data between $AP_0$ and $AP_1$ is 1360, the pulse count of encoder data between $AP_0$ and $AP_2$ is 2700, and the pulse count of encoder data between $AP_0$ and $AP_3$ is 4060. Since the speed of rotation in encoder data is stable and is free from influence of external factors such as a belt slip, it can be considered that no positioning error exists if the pulse count of corresponding encoder data of an AP signal is utilized to position the X-ray tube 12. The calculated pulse counts are fine-tuned according to practical experience (for example, 1360 is fine-tuned to 1350, 2700 to 2708 and 4060 to 4070 . . . ) and are saved in a table as table data, as indicated by TD in Table 2. During the positioning of the X-ray tube 12, the motor controller 13 utilizes the AP signals recorded in the data table and the corresponding pulse count of encoder data to calibrate the actual position of the X-ray tube 12.

The motor controller 13 is further configured to communicate with a storage device or memory (not shown). The storage device is used to store encoder data containing AP signals calculated by the motor controller 13. The storage device includes various computer memories for storing data. The storage device may be an independent component relative to the motor controller 13. However, it should be understood that the storage device may be an integrated part of the motor controller 13. The motor controller 13 is further configured to utilize encoder data containing AP signals stored in the storage device to control the running of the motor 14 so as to control the position of the X-ray tube 12.

Figure 3:
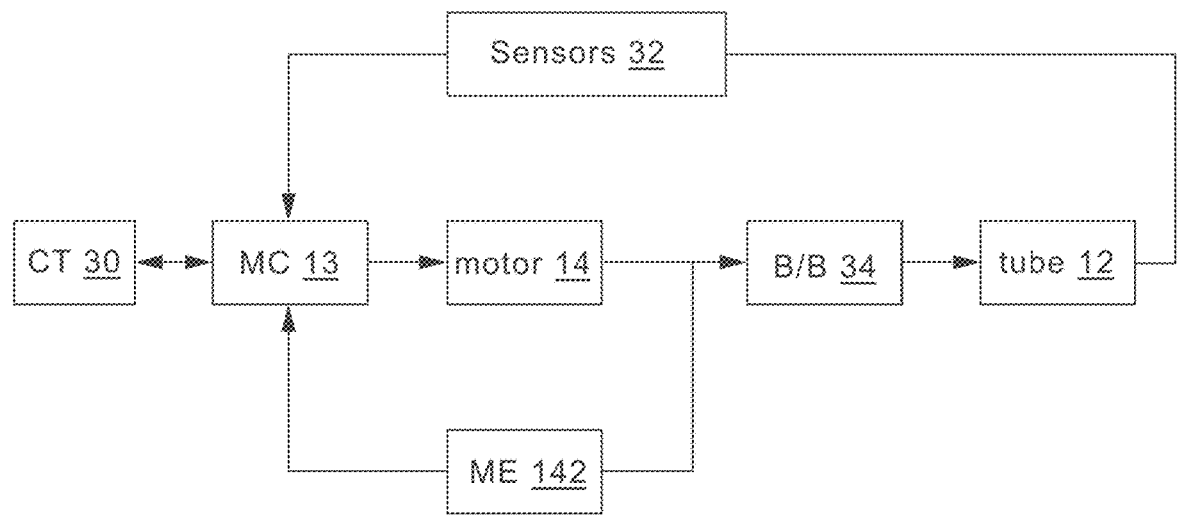
FIG. 3 shows the closed-loop control of the rotation of the gantry according to an exemplary embodiment of the disclosure.

FIG. 3 shows the closed-loop control of the rotation of the gantry according to one exemplary embodiment of the disclosure. In one exemplary embodiment of the disclosure, when the gantry rotates clockwise, the check points move toward the AP and IP sensors 32 one by one at certain intervals, wherein the AP sensor of the AP and IP sensors 32 generate n high-level signals in turn, while the IP sensor outputs one high-level signal when the distance between the reference check point and the IP sensor is greater than a preset reference detectable distance, and as the reference check point moves away, the IP sensor outputs low-level signals all the time until the current period ends. The AP and IP sensor 32 inputs detected AP signals and IP signals into the motor controller 13. The encoder data in the motor encoder 142 is also input into the motor controller 13. The motor controller 13 controls the running of the motor 14 to further control the positions of the belt/bearing 34 and the X-ray tube 12 based on the AP signal acquired from the AP sensor, the IP signal acquired from the IP sensor and encoder data acquired from the motor encoder 142. The motor controller 13 also controls other operations of the CT scanner 30, for example, steering.

FIG. 4 shows the structure of the device of controlling the position of the X-ray tube of a CT system according to one exemplary embodiment of the disclosure. As shown in FIG. 4, the position device 40 comprises an acquisition module (input) 42, a determination module (homing positioning signal generator) 44, a calculation module (calculator) 46 and a control module (controller) 48. In an exemplary embodiment, the device 40 includes processing circuitry that is configured to perform one or more functions and/or operations of the device 40. Additionally or alternatively, one or more of the components of the device 40 include processing circuitry that is configured to perform one or more respective functions and/or operations of the component(s). In an exemplary embodiment, the various modules of the device 40 store corresponding instructions that are executable by one or more processors of the device 40, that when executed by the processor(s) performs the respective functions of the module(s). In an exemplary embodiment, one or more of the modules includes a corresponding processor that is configured to perform the corresponding functions and/or operations of the module(s). In an exemplary embodiment, the module(s) include executable instructions and are within one or more processors, where the instructions of the modules correspond to various functions performed by the processor(s) when executed by the processor(s).

In one exemplary embodiment of the disclosure, the acquisition module 42 is configured to acquire an AP signal output by an AP sensor of the CT system, an IP signal output by an IP sensor and encoder data output by a motor, the determination module 44 is configured to determine a homing positioning signal $AP_0$ of the AP signal based on the AP signal and the IP signal, wherein the homing positioning signal $AP_0$ is used to determine the starting point of the period of rotation of the X-ray tube, the calculation module 46 is configured to utilize the encoder data to calculate the encoder data containing AP signal based on the determined homing positioning signal $AP_0$, wherein the encoder data containing AP signal is the AP signal calibrated by use of the encoder data, and the controller 48 is configured to control the position of the X-ray tube based on the encoder data containing AP signal.

In one exemplary embodiment of the disclosure, the determination module 44 is further configured to detect whether the current IP signal is a high-level signal, and determine the high-level signal of the AP signal in the period in which the current IP signal is continuously a high-level signal to be the homing positioning signal $AP_0$ if the current IP signal is a high-level signal. The calculation module 46 is further configured to detect each high-level signal $AP_i$ of the AP signal in the period from the homing positioning signal $AP_0$ to when the IP signal is a high-level signal again, respectively calculate the pulse count of the encoder data in the time segment between the homing positioning signal $AP_0$ and each high-level signal $AP_i$, and save the correspondence between the calculated pulse count of the encoder data and the AP signal as an encoder data containing AP signal. The controller is further configured to read the saved encoder data containing AP signal during the rotation of the gantry of the CT system, and utilizing the encoder data containing AP signal to calibrate the position of the X-ray tube so as to control the position of the X-ray tube.

Through the above-mentioned structure, without any sensing device or component added, the position of the X-ray tube is calibrated by use of the pre-adjustment mode during the subsequent operation, and thus the precision of positioning the X-ray tube is improved.

FIG. 5 is a flowchart of the method of controlling the position of the X-ray tube of the CT system according to one exemplary embodiment of the disclosure. As shown in FIG. 5, the method comprises the following steps:

Step S502: Acquire an AP signal output by an AP sensor of the CT system, an IP signal output by an IP sensor and encoder data output by a motor.

When the distance between the AP sensor and any check point is less than a preset detectable distance, the AP sensor will sense the check point and generate a high-level signal, and when the distance is greater than the detectable distance, the AP sensor will fail to sense the check point and generate a low-level signal. When the distance between the IP sensor and the reference check point is less than a preset reference detectable distance, the IP sensor will sense the reference check point and generate a high-level signal, and when the distance is greater than the reference detectable distance, the IP sensor will fail to sense the reference check point and generate a low-level signal. The motor outputs encoder data representing the speed of rotation of the gantry. The AP signal, IP signal and encoder data are all transmitted to the motor controller.

Step S504: Determine a homing positioning signal $AP_0$ of the AP signal based on the AP signal and the IP signal, wherein the homing positioning signal $AP_0$ is used to determine the starting point of the period of rotation of the X-ray tube.

One rotation (namely, 360 degrees) of the X-ray tube around the central axis of the gantry is a period. When the distance between the reference check point and the IP sensor reaches a preset reference detectable distance, the IP sensor generates a high-level response signal. At this time, the distance between the check point and the AP sensor also reaches the preset detectable distance and the AP sensor generates a high-level signal. The high-level signal generated by the AP sensor is denoted by $AP_0$ and is used as the starting point of a rotation period.

Step S506: Utilize the encoder data to calculate the encoder data containing AP signal based on the determined homing positioning signal $AP_0$, wherein the encoder data containing AP signal is the AP signal calibrated by use of the encoder data.

After determining the $AP_0$ signal, the motor controller utilizes the encoder data to calculate the pulse count of encoder data between AP signals, starting from $AP_0$. As shown in FIG. 2, the pulse count of encoder data between $AP_0$ and $AP_1$ is 1360, the pulse count of encoder data between $AP_0$ and $AP_2$ is 2700, and the pulse count of encoder data between $AP_0$ and $AP_3$ is 4060.

Step S508: Save encoder data containing AP signals in a table.

The calculated pulse counts are fine-tuned according to practical experience (for example, 1360 is fine-tuned to 1350, 2700 to 2708 and 4060 to 4070 . . . ) and are saved in the table as table data.

Steps S502 to S508 are performed in the commissioning stage.

Step S510: Control the position of the X-ray tube based on the encoder data containing AP signal.

During the positioning of the X-ray tube 12, the motor controller 13 utilizes the AP signals recorded in the data table and the corresponding pulse count of encoder data to calibrate the actual position of the X-ray tube 12. This step is performed in the formal running stage of the CT scanner.

The exemplary embodiments of the disclosure further provide a storage medium, and a computer program is stored in the storage medium. When executed, the computer program enables a processor to execute the method of controlling the position of the X-ray tube of the CT system in the embodiments of the disclosure.

In the above-mentioned embodiment, the above-mentioned storage medium includes, but is not limited to a USB disk, read-only memory (ROM), random access memory (RAM), mobile harddisk, magnetic disk or optical disk and other various media which can store program codes.

It should be understood that the technical content disclosed in the embodiments of the disclosure can be realized in other ways. The above-described embodiments of the device are given only for illustrative purposes. The division of units or modules is only a logical function division, and other division methods may be used in the actual realization. For example, a plurality of units or modules or components may be combined or integrated into another system, or some features may be ignored or may not be executed. In addition, the shown or discussed couplings, or direct couplings or communication connections between them may be indirect couplings or communication connections, electrical or otherwise, through some interfaces, modules or units.

The unit or module described as a separate part may be or may not be physically separated, and the part shown as a unit or module may be or may not be a physical unit or module, that is to say, it may be located at one place or may be distributed to a plurality of network units or modules. Part or all of the units or modules may be selected to realize the solution of the embodiment according to the actual requirements.

In addition, the functional units or modules in each embodiment of the disclosure may be integrated into a processing unit or module, or each unit or module may physically exist separately, or two or more units or modules may be integrated into a unit or module. The above-mentioned integrated unit or module may be realized in the form of hardware or in the form of a software functional unit or module.

The integrated unit may be stored in a computer-readable storage medium if it is realized in the form of a software functional unit and is marketed or used as an independent product. Based on such an understanding, the technical solution of the disclosure or the part which makes contributions to the prior art, or all or part of the technical solution may essentially be represented in the form of a software product, and the computer software product is stored in a storage medium and comprises a plurality of instructions to enable a computer (PC, server or network equipment) to execute all or part of the steps of the method described in the embodiments of the disclosure. The above-mentioned storage medium includes a USB disk, read-only memory (ROM), random access memory (RAM), mobile harddisk, magnetic disk or optical disk and other various media which can store program codes.

Only preferred embodiments of the present disclosure are described above. It should be pointed out that those skilled in the art can make improvements and modifications without departing from the principle of the disclosure and these improvements and modifications should also fall within the scope of protection of the disclosure.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processing circuitry" shall be understood to be circuit(s) or processor(s), or a combination thereof. A circuit includes an analog circuit, a digital circuit, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

REFERENCE LIST

100: CT system
10: AP sensor
11: IP sensor
12: X-ray tube
13: Motor controller
14: Motor
15: Gantry
16: Check point
17: Reference check point
18: Tension pulley
AP: AP signal
TD: Table data
ED: Encoder data
30: CT scanner
32: AP & IP sensors
34: Belt/bearing
142: Motor encoder
40: Device
42: Acquisition module
44: Determination module
46: Calculation module
48: Controller

The invention claimed is:

1. A method of controlling the position of an X-ray tube of a computed tomography (CT) system, comprising:
acquiring an angular position (AP) signal output by an AP sensor of the CT system, an index pulse (IP) signal output by an IP sensor, and encoder data output by a motor,
determining a homing positioning signal of the AP signal based on the AP signal and the IP signal, wherein a starting point of a period of rotation of the X-ray tube is determinable based on the homing positioning signal,
calibrating the AP signal based on the determined homing positioning signal and the encoder data to determine a calibrated AP signal, and
controlling the position of the X-ray tube based on the calibrated AP signal.

2. The method as claimed in claim 1, wherein:
the AP signal is based on a detection, by the AP sensor, of a plurality of check points arranged at even intervals on an outer circumferential surface of a gantry of the CT system,
the IP signal is based on a detection, by the IP sensor, of a reference check point arranged on the outer circumferential surface of the gantry of the CT system, the period of rotation of the X-ray tube being determined based further on the IP signal, and/or
the encoder data is data output by the encoder of the motor, a speed of rotation of the X-ray tube being controlled based on the encoder data.

3. The method as claimed in claim 1, wherein determining the homing positioning signal of the AP signal comprises:
detecting a signal level of the IP signal, and
in response to the IP signal having a first IP signal level value that is greater than a second IP signal level value, determining the homing positioning signal to be the AP signal having a first AP signal level value, which is greater than a second AP signal level value, in a period in which the IP signal continuously has the first signal level value.

4. The method as claimed in claim 3, wherein determining the calibrated AP signal comprises:
detecting each first AP signal level value of the AP signal in the period from the homing positioning signal to when the IP signal again has the first IP signal level value,
respectively calculating a pulse count of the encoder data in a time segment between the homing positioning signal and each first AP signal level value of the AP signal, and
saving the correspondence between the calculated pulse count of the encoder data and the AP signal as the calibrated AP signal.

5. The method as claimed in claim 4, wherein controlling the position of the X-ray tube based on the calibrated AP signal comprises:
reading the calibrated AP signal during the rotation of the gantry of the CT system, and
utilizing the calibrated AP signal to calibrate the position of the X-ray tube so as to control the position of the X-ray tube.

6. The method as claimed in claim 3, wherein:
the first IP signal level value being indicative of a detection by the IP sensor and the second IP signal level value being indicative of a lack of the detection by the IP sensor; and
the first AP signal level value being indicative of a detection by the AP sensor and the second AP signal level value being indicative of a lack of the detection by the AP sensor.

7. A non-transitory computer-readable storage medium with an executable program stored thereon, that when executed, instructs a processor to perform the method of claim 1.

8. The method as claimed in claim 1, wherein the AP signal is based on a detection, by the AP sensor, of a plurality of check points arranged at even intervals on an outer circumferential surface of a gantry of the CT system.

9. The method as claimed in claim 1, wherein the IP signal is based on a detection, by the IP sensor, of a reference check point arranged on the outer circumferential surface of the gantry of the CT system, the period of rotation of the X-ray tube being determined based further on the IP signal.

10. The method as claimed in claim 1, wherein:
the AP signal is based on a detection, by the AP sensor, of a plurality of check points arranged at even intervals on an outer circumferential surface of a gantry of the CT system; and
the IP signal is based on a detection, by the IP sensor, of a reference check point arranged on the outer circumferential surface of the gantry of the CT system, the period of rotation of the X-ray tube being determined based further on the IP signal.

11. The method as claimed in claim 1, wherein the encoder data is data output by the encoder of the motor, a speed of rotation of the X-ray tube being controlled based on the encoder data.

12. A device of controlling the position of an X-ray tube of a computed tomography (CT) system, comprising:
a memory storing executable instructions; and
a processor configured to execute the instructions to:
acquire an angular position (AP) signal output by an AP sensor of the CT system, an index pulse (IP) signal output by an IP sensor and encoder data output by a motor,
determine a homing positioning signal of the AP signal based on the AP signal and the IP signal, wherein a starting point of a period of rotation of the X-ray tube is determinable based on the homing position signal,
calibrate the AP signal based on the determined homing positioning signal and the encoder data to determine a calibrated AP signal, and
control the position of the X-ray tube based on the calibrated AP signal.

13. The device as claimed in claim 12, wherein the processor is further configured to:
detect a signal level of the IP signal, and
in response to the IP signal having a first IP signal level value that is greater than a second IP signal level value, determine the homing positioning signal to be the AP signal having a first AP signal level value in a period in which the IP signal continuously has the first IP signal level value.

14. The device as claimed in claim 12, wherein the processor is further configured to:
detect each first AP signal level value of the AP signal in the period from the homing positioning signal to when the IP signal again has the first IP signal level value,
respectively calculate a pulse count of the encoder data in a time segment between the homing positioning signal and each first AP signal level value of the AP signal, and
save the correspondence between the calculated pulse count of the encoder data and the AP signal as the calibrated AP signal.

15. The device as claimed in claim 12, wherein the processor is further configured to:
read the calibrated AP signal during the rotation of the gantry of the CT system, and
utilize the calibrated AP signal to calibrate the position of the X-ray tube so as to control the position of the X-ray tube.

16. A computed tomography (CT) system, comprising:
a gantry,
an angular position (AP) sensor configured to detect a plurality of check points arranged at even intervals on the outer circumferential surface of the gantry to acquire an AP signal,
an index pulse (IP) sensor configured to detect a reference check point arranged on the outer circumferential surface of the gantry to acquire an IP signal,
a motor configured to output encoder data of the motor, and
the device as claimed in claim 12.

* * * * *